United States Patent [19]

Christinger

[11] Patent Number: 4,500,310
[45] Date of Patent: Feb. 19, 1985

[54] VARIABLE SEALING PRESSURE PLUNGER ROD ASSEMBLY

[75] Inventor: Werner Christinger, Franklin Lakes, N.J.

[73] Assignee: Becton, Dickinson and Company, Paramus, N.J.

[21] Appl. No.: 451,307

[22] Filed: Dec. 20, 1982

[51] Int. Cl.³ .............................................. A61M 5/00
[52] U.S. Cl. .................................... 604/228; 604/230
[58] Field of Search ........................ 604/218, 228, 230

[56]  References Cited

U.S. PATENT DOCUMENTS

| 422,437 | 3/1890 | Otto | 604/230 X |
|---|---|---|---|
| 2,895,773 | 7/1959 | McConnaughey | |
| 3,628,523 | 12/1971 | Pirtle, Jr. | 604/230 |
| 3,635,218 | 1/1972 | Ericson | |
| 3,828,778 | 8/1974 | Weinhart | 604/228 |
| 4,074,715 | 2/1978 | Geiger | 604/230 |
| 4,180,069 | 12/1979 | Walters | 604/228 |

FOREIGN PATENT DOCUMENTS 78213  5/1962  France ................. 604/228

*Primary Examiner*—John D. Yasko
*Attorney, Agent, or Firm*—John L. Voellmicke

[57] ABSTRACT

A variable sealing pressure plunger rod assembly for use with a syringe barrel comprises a plunger rod and a flexible stopper. The plunger rod includes a rigid elongate shaft portion having a circular tapered tip portion at the distal end thereof. The flexible cup-shaped stopper includes an annular side wall and a front wall connected to the side wall. An exterior surface of the side wall is larger in diameter than the syringe barrel inside diameter. The stopper interior includes an inside surface of the front wall and a tapered annular inside wall connected to the side wall and to the inside surface. This tapered annular inside wall and the inside surface define a cavity which has the tapered tip portion received therein. The tapered annular inside wall and the tapered tip portion are inclined at approximately the same angle and adjacent to each other. Cooperating structure for maintaining the positional relationship of the stopper and the plunger rod is also provided.

A method of using a syringe assembly including the variable sealing pressure plunger rod assembly, substantially as described above, is also within the purview of the present invention.

27 Claims, 14 Drawing Figures

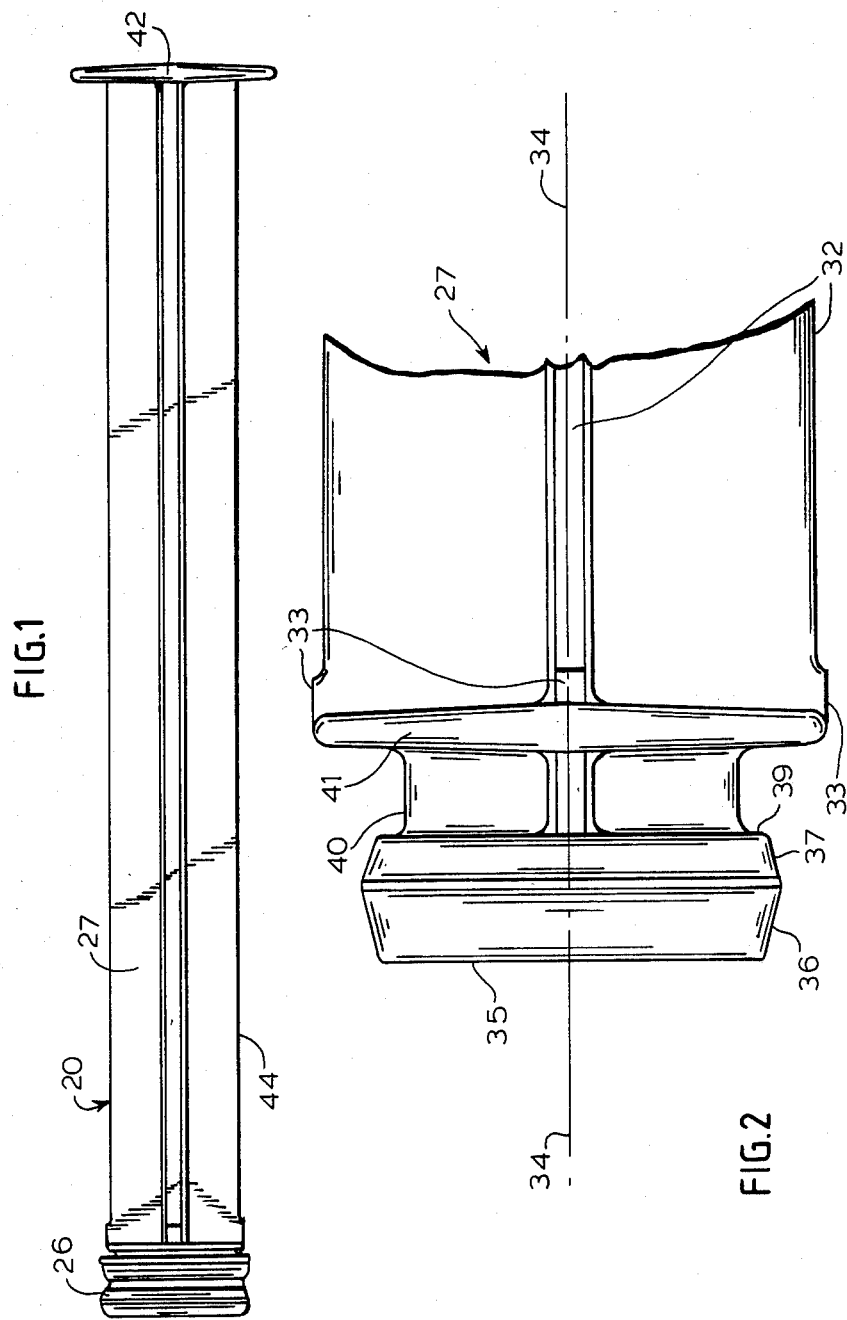

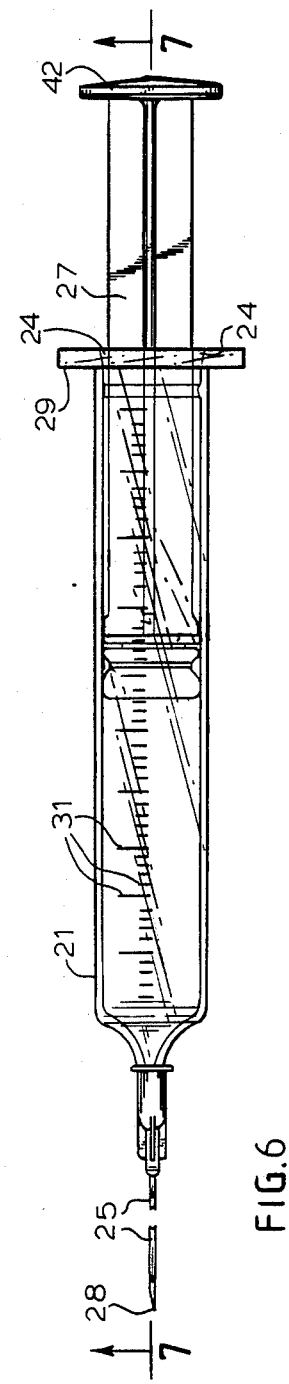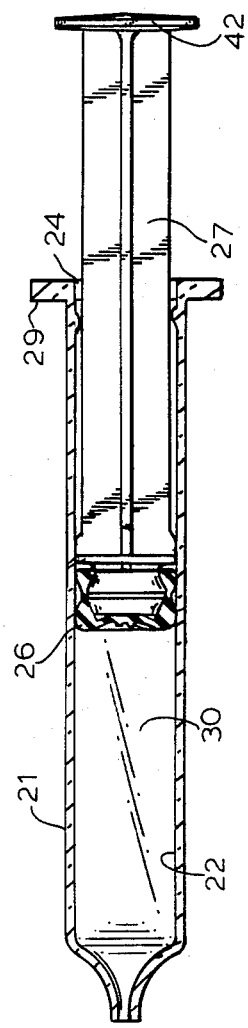
FIG.6
FIG.7

VARIABLE SEALING PRESSURE PLUNGER ROD ASSEMBLY

FIELD OF THE INVENTION

The present invention relates to an apparatus and method for moving fluid along a conduit, and more particularly concerns a variable sealing pressure plunger rod assembly for use in a syringe and its method of use.

DESCRIPTION OF THE PRIOR ART

Generally speaking, a hypodermic syringe consists of a cylindrical barrel, most commonly made of thermoplastic material such as polypropylene, with a distal end adapted to be connected to a hypodermic needle and a proximal end adapted to receive a stopper and plunger rod assembly. One of the purposes of the stopper is to provide a relatively air tight seal between itself and the syringe barrel so that movement of the stopper up and down the barrel will cause liquid medication, blood or other fluids to be drawn into or forced out of the syringe through the distal end. The stopper is moved along the syringe barrel by applying axial force to the rigid plunger rod which is connected to the stopper and is sufficiently long as to be accessible outside of the barrel. The stopper should be sufficiently flexible so that it will seal the inside diameter of the barrel without requiring excessive force to move it up and down the barrel.

In order to assure an air tight seal between the syringe barrel and the stopper, known prior art stoppers are manufactured with a larger outside diameter than the inside diameter of the syringe barrels they will be used in. The syringe-stopper combination is designed such that the stopper, when introduced into the syringe barrel, is compressed enough to provide adequate pressure between the syringe and the stopper to seal this interface. As a result of this configuration, the interface of the stopper and the syringe barrel maintains, at all times, a sealing pressure capable of withstanding the challenges of filling and injecting even though this magnitude of sealing pressure is not required when the syringe is not in use.

The stopper is chemically stable so that undesirable amounts of the various chemical components of the stopper do not enter the liquid contained in the syringe. Since hypodermic syringes are frequently used to inject medication into a human body or to withdraw blood for subsequent analysis it is not desirable to have stoppers introduce foreign substances which can adversely affect the patient or the blood analysis. Hypodermic syringe stoppers are most commonly made of materials such as natural rubber or butyl rubber. Although the rubber stoppers have desirable physical properties they possess a number of disadvantages. For example, rubber stoppers contain additional chemical components such as fillers and vulcanizing accelerators which can exude to the surface and contact the liquid in the syringe wherein blood test results or medication efficacy may be affected. The problem is further aggravated when there is long term storage of liquid medication in the hypodermic syringe. Also, rubber stoppers are expensive to manufacture due to the long mold cycle time required by the vulcanization step which takes place while the stoppers are in the mold.

Recognizing the above-mentioned deficiencies in rubber stoppers, it is desirable to provide a syringe stopper made of a thermoplastic material. Normally, thermoplastic stoppers are less expensive to manufacture due to shorter molding cycle times which result in improved productivity of the molding machinery. The undesirable effects of fillers and vulcanizing agents on the liquid contents of the syringe would be eliminated since these rubber additives are not necessary in the production of thermoplastic stoppers. Also, the complexity of drug compatability testing may be greatly reduced when thermoplastic syringe stoppers are used since both the barrel and the stopper may be constructed of materials that have similar chemical properties. In addition, the thermoplastic stopper may provide improved stability and increased shelf life for liquid medications stored in the syringe.

A major disadvantage of using a thermoplastic stopper is that over a period of time the stopper can achieve a compression set. That is, the stresses of the interference fit between the stopper and the syringe barrel can cause cold flow of the thermoplastic stopper material and thus the outside diameter of the stopper can become reduced and the stopper may no longer effectively seal the contents of the syringe.

With the above-mentioned deficiencies in mind, it is desired to provide a hypodermic syringe plunger rod assembly which is designed so that a thermoplastic stopper may be used and wherein the stopper will not be adversely affected by compression set after assembly in the syringe barrel. It is further desired to provide a thermoplastic syringe stopper which can provide increased chemical stability in order to improve long term storage capabilities, reduce interaction with liquids in the syringe and reduce the complexity of drug compatability testing. It is also desired to provide a syringe stopper that can be manufactured with reduced cycle times on conventional injection molding equipment.

SUMMARY OF THE INVENTION

The plunger rod assembly of the present invention is useful for drawing fluid into or pushing fluid out of a receptacle having an inside wall and provided with means for receiving the plunger rod assembly and means for fluid communication with the exterior of the receptacle. This plunger rod assembly comprises a plunger rod and a flexible stopper. A plunger rod includes a rigid elongate shaft portion having a circular tapered tip portion at its distal end. A flexible cup-shaped stopper includes an annular side wall and a front wall connected to the side wall. An exterior surface of the side wall is larger in diameter than the receptacle inside wall. The interior of the stopper includes an inside surface of the front wall and a tapered annular inside wall which is connected to the annular side wall. This tapered annular inside wall and the inside surface of the front wall are connected and define a cavity which has the tapered tip portion of the plunger rod received therein. Also, the tapered annular inside wall of the stopper is inclined at approximately the same angle as the tapered tip portion of the plunger rod and located adjacent thereto. This embodiment also contains a cooperating means for maintaining the positional relationship of the stopper and the plunger rod.

Another embodiment of the plunger rod assembly of the present invention consists of a plunger rod and a stopper for use with a syringe barrel. The syringe barrel contains a cylindrical inside wall with a proximal open end to receive the plunger rod assembly and a distal end adapted to receive and be in fluid communication with fluid delivery means such as a hypodermic needle. A plunger rod includes a rigid elongate shaft portion having a circular tapered tip portion at the distal end thereof. The shaft portion is sufficiently long as to be accessible outside of the syringe barrel. A flexible stopper includes an annular side wall circumscribing a longitudinal axis and a front wall intersecting the longitudinal axis and being integral with the side wall. An annular rib, which is larger in diameter than the side wall, is integral with the side wall. This rib is also larger in diameter than the syringe barrel cylindrical inside wall. The interior of the stopper includes an inside surface of the front wall and a tapered annular inside wall extending from the inside surface and being integral with the side wall. The tapered annular inside wall and the inside surface define a cavity which has the tapered tip portion received therein. Also, the tapered annular inside wall is inclined at approximately the same angle as the tapered tip portion and is positioned adjacent thereto.

Another aspect of the present invention is a plunger rod for use with a flexible stopper to form a variable sealing pressure plunger rod assembly. This plunger rod contains a rigid elongate shaft portion which defines a longitudinal axis. At the distal end of the shaft portion there is a flat surface which lies in a plane that is substantially perpendicular to the longitudinal axis. A tapered wall intersects the flat surface and extends from this intersection along the longitudinal axis until it ends at a rear portion. This rear portion of the tapered wall projects inwardly from the tapered wall and is in a plane substantially perpendicular to the longitudinal axis. Means for holding a stopper in a positional relationship with the tapered wall is also provided.

Still another aspect of the present invention is a flexible stopper for use on a plunger rod to form a variable sealing pressure plunger rod assembly. This stopper contains an annular side wall defining a longitudinal axis, and a front wall intersecting the longitudinal axis and connected to the side wall. An annular rib, which is larger in diameter than the annular side wall, is connected to the annular side wall. The interior of the stopper consists of an inside surface of the front wall, and a tapered annular inside wall which extends from the inside surface and is positioned around the longitudinal axis adjacent to the annular rib.

A further embodiment of the present invention is a syringe assembly. This syringe assembly consists of a syringe barrel, a plunger rod, and a flexible stopper. A syringe barrel contains a cylindrical inside wall, an open end at the proximal end of the the barrel and a distal end in fluid communication with the exterior of the syringe barrel. The plunger rod includes a rigid shaft portion having a circular tip portion at the distal end thereof. A flexible stopper is contained within the syringe barrel. This stopper comprises an annular side wall, a front wall connected to the side wall, and an exterior surface of the side wall which is larger in diameter than the cylindrical inside wall. The annular side wall and the front wall define a receptacle which has the tip portion of the plunger rod received therein. Also provided is a means for creating a force component of a force applied along the shaft portion. This force component is directed radially outwardly toward the exterior surface of the stopper. Further, means for maintaining the positional relationship of the stopper and the tip portion is provided.

A still further aspect of the present invention is a method of expelling liquid from a syringe assembly. This syringe assembly comprises a barrel and a plunger rod assembly which consists of a plunger rod and a stopper. The barrel consists of an inside wall, a proximal end to receive a plunger rod assembly and a distal end in fluid communication with the exterior of the syringe. An elongate plunger rod defines a longitudinal axis with a circular tapered tip at one end thereof, the tapered tip being smallest at the distal end of the plunger rod and tapering outwardly along the longitudinal axis. A flexible cup-shaped stopper includes an annular side wall with an exterior surface which is larger in diameter than the syringe barrel inside wall. A tapered annular inside wall is connected to the annular side wall and is inclined at approximately the same angle as the tapered tip and is positioned adjacent to the tapered tip. In accordance with this aspect of the invention the method comprises applying a driving force along the elongate plunger rod in the direction of the stopper whereby the applied force creates a force component which is directed substantially outwardly from the interface of the tapered tip and the tapered annular inside wall. As a result of the outwardly directed force component the exterior surface applies more sealing pressure to the syringe barrel inside wall than the pressure existing as a result of the exterior surface being larger than the syringe barrel inside wall. Simultaneously, a component of the applied driving force along the plunger rod moves the stopper and the fluid contained in the syringe along the barrel to the exterior of the syringe.

In accordance with the principles of the present invention a number of advantages and objectives are achieved. The present invention allows an initial interference fit of less normal force between the outside wall of the stopper and the syringe barrel inside wall of an assembled syringe than the interference fit of the components of known syringe assemblies. With the present invention it is only necessary to have an initial interference fit which creates sufficient pressure to contain a fluid in the syringe. The initial interference fit does not have to create enough pressure to allow drawing fluid into the syringe or expelling fluid from the syringe without leakage between the stopper and the syringe barrel since the present invention increases the sealing pressure when a driving force is applied along the plunger rod. This lower initial interference fit results in lower stresses in the stopper when it is assembled in the syringe barrel. Therefore, a thermoplastic syringe stopper may be used since the possibility of compression set, which will adversely affect the function of a syringe with a thermoplastic stopper, is reduced. Accordingly, the present invention provides for the use of a syringe stopper which does not have fillers and vulcanizing agents and is therefore less likely to interact with or contaminate the contents of the syringe. The thermoplastic syringe stopper offers the potential for increased shelf life for drugs which are packaged in the syringe and reduces the potential for adversely affecting the results of laboratory tests involving fluid from the syringe. A reduction in the complexity and the time required for drug compatability testing is now possible since both the syringe barrel and the stopper can be made of thermoplastic materials. Also, increased productivity is possible due to the lower manufacturing cycle time of injection molded thermoplastics with respect to compression molded rubber parts.

BRIEF DESCRIPTION OF THE DRAWINGS

FIG. 1 is a side elevation view of a preferred plunger rod assembly of the present invention;

FIG. 2 is an enlarged side elevation view of the distal end of a plunger rod of the preferred plunger rod assembly of the present invention;

FIG. 6 is a side elevation view of a syringe assembly containing the preferred plunger rod assembly of the present invention;

FIG. 7 is a partial cross-sectional view of the syringe assembly of FIG. 6 taken along line 7—7 thereof;

DETAILED DESCRIPTION

Figure 3:
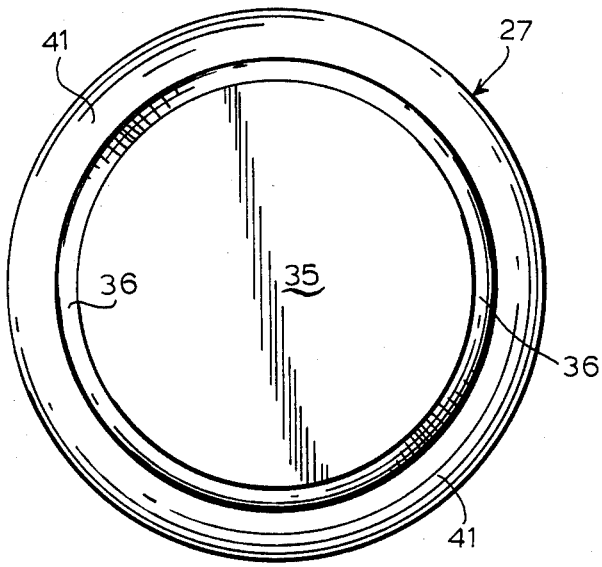
FIG. 3 is an enlarged front elevation view of the distal end of the plunger rod of FIG. 2.

While this invention is satisifed by embodiments in many different forms, there is shown in the drawings and will herein be described in detail preferred embodiments of the invention with the understanding that the present disclosure is to be considered as exemplary of the principles of the invention and is not intended to limit the invention to the embodiments illustrated. The scope of the invention will be measured by the appended claims and their equivalents.

The plunger rod assembly of the present invention has many uses and one such use is in a syringe as described hereinafter.

Turning to FIGS. 1-5 and to FIG. 1 in particular, the preferred embodiment of the variable sealing pressure plunger rod assembly of the present invention is illustrated. A plunger rod assembly 20 generally includes a flexible stopper 26 and a plunger rod 27.

As best shown in FIGS. 1-3 plunger rod 27 includes an elongate shaft portion 32 defining a longitudinal axis 34. A front portion 35 is located at the distal end of the shaft portion. This front portion is preferably a flat surface in a plane substantially perpendicular to the longitudinal axis. A circular forward tapered plunger rod wall 36 intersects the front portion and tapers outwardly from this intersection along longitudinal axis 34. A circular rear tapered plunger rod wall 37 is connected to the forward tapered plunger rod wall and is tapered inwardly from this connection along longitudinal axis 34 until it terminates at a rear portion 39. The rear portion is substantially in a plane intersecting the longitudinal axis. An undercut neck portion 40 is connected to rear portion 39 and to structural flange 41.

A disc shaped member 42 is provided at the proximal end of the elongate shaft portion of the plunger rod. It is desirable that the disc shaped member be substantially perpendicular to longitudinal axis 34 and that it be larger in diameter than the largest dimension of the elongate shaft portion taken in a plane perpendicular to longitudinal axis 34. Disc shaped member 42 is a convenient structure for applying forces to move the plunger rod with respect to the syringe barrel. A central portion 44 of the plunger rod is contained between structural flange 41 and disc shaped member 42. The central portion may assume a variety of cross-sectional shapes including circular or a plus sign shaped rib structure. It is desirable that the central portion be almost as large as the inside diameter of the syringe barrel so that it will assist in keeping the plunger rod assembly concentrically aligned within the syringe barrel. It is preferred that plunger rod 27 be of one piece construction, however, it is within the purview of this invention to include multipiece plunger rods, such as the type used with some prefilled syringes, which are assembled at the time of use.

Figure 4:
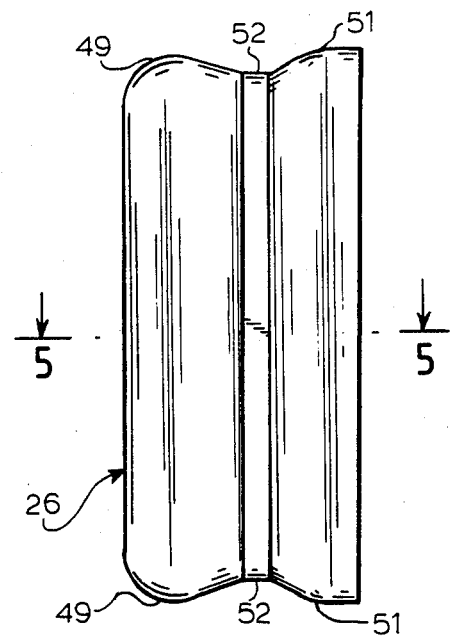
FIG. 4 is an enlarged side elevation view of a flexible stopper of the preferred plunger rod assembly of the present invention.
Figure 5:
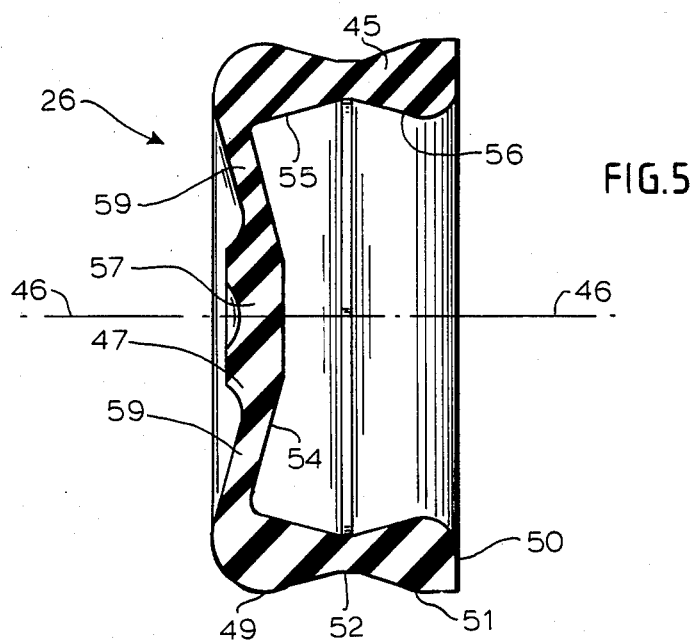
FIG. 5 is an enlarged cross-sectional view of the stopper of FIG. 4 taken along line 5—5.

As best illustrated in FIGS. 4 and 5, flexible stopper 26 includes an annular side wall 45 circumscribing a stopper longitudinal axis 46. A front wall 47 intersects the stopper longitudinal axis and is integral with the side wall. An annular exterior front rib 49 is formed at the intersection of the front wall and the side wall. An annular rear edge 50 is located at the end opposite the front wall and is integral with the annular side wall. An annular exterior rear rib 51 is formed at the intersection of the side wall and the rear edge, with front rib 49 and rear rib 51 being larger in diameter than the syringe barrel inside wall. Also, an annular exterior recess 52 is positioned between and is of smaller diameter than the front rib and the rear rib.

The interior of stopper 26 includes a front inside surface 54 of front wall 47 and a forward tapered annular inside wall 55 which intersects the front inside surface and is tapered outwardly from this intersection along stopper longitudinal axis 46. The forward tapered annular inside wall is inclined at approximately the same angle as forward tapered plunger rod wall 36 and lies adjacent thereto when the stopper and the plunger rod are assembled (as seen by briefly referring to FIGS. 7-9). The interior of stopper 26 also contains a rear tapered annular inside wall 56 connected to the forward tapered annular inside wall and tapered inwardly from this connection along the stopper longitudinal axis and terminating at rear edge 50. The rear tapered annular inside wall is inclined at approximately the same angle as rear tapered plunger rod wall 37 and lies adjacent thereto when the stopper and the plunger rod are assembled. Forward tapered annular inside wall 55 and rear tapered annular inside wall 56 are both preferably integral with annular side wall 45.

Turning now to FIGS. 6-7, the plunger rod assembly of the present invention is incorporated in a syringe barrel 21 having a cylindrical inside wall 22. This syringe barrel is provided with a proximal open end 24 to receive the plunger rod assembly and a distal end adapted to receive and be in fluid communication with fluid delivery means, such as a hypodermic needle 25. The syringe barrel usually includes a flange 29 which is a convenient structure for holding the syringe when the plunger rod is being moved in and out to draw fluids into or expel fluids from the interior of the barrel 30. Many syringe barrels contain a printed scale 31 on the exterior of the barrel so that the user may determine the amount of fluid drawn into or expelled from the syringe.

In use, a hypodermic syringe with needle attached, as shown in FIG. 6, may be filled with liquid medication from a known and available vial, which is not shown. The syringe is filled by piercing and penetrating the pierceable closure of a vial containing the medication with hypodermic needle 25 and manually pushing the plunger rod so that the stopper moves toward the needle thus forcing air into the vial and increasing the air pressure in the vial. Then, with needle tip 28 submerged in the liquid medication, the stopper is withdrawn by pulling the plunger rod so that the medication is drawn through the needle into the syringe. The filled syringe is then used to inject medication into the patient by piercing and penetrating the desired area of the patient's body with the hypodermic needle and then applying manual force to the plunger rod in order to move the stopper along the inside wall of the syringe and force the medication through the needle into the patient.

The pressure exerted by a stopper on the inside wall of a syringe must be large enough to adequately seal this interface in order to prevent liquid medication from escaping while it is being injected into the patient and to prevent air from entering the interior of the syringe barrel when medication is being drawn into the syringe from a medication vial.

Figure 8:
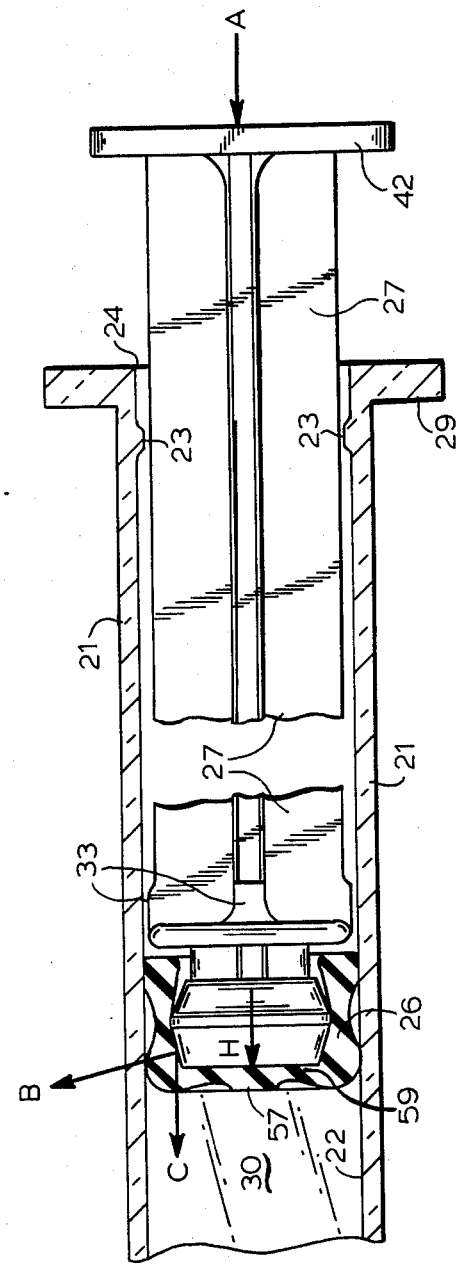
FIG. 8 is an enlarged partial side view of FIG. 7 showing selected forces in action when the preferred plunger rod assembly of the present invention is used to expel fluid from a syringe barrel.
Figure 9:
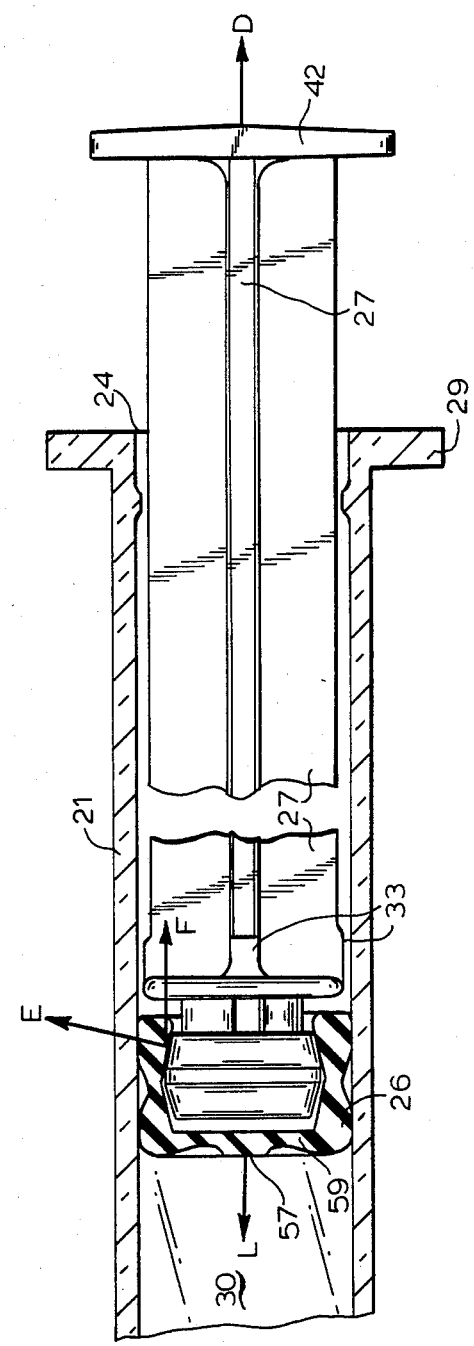
FIG. 9 is an enlarged partial side view of FIG. 7 showing selected forces in action when the preferred plunger rod assembly of the present invention is used to draw fluid into a syringe barrel.

Referring to FIGS. 1-9 with particular emphasis on FIGS. 8-9, variable sealing pressure plunger rod assembly 20 of the present invention, when assembled in a syringe barrel, functions as follows. When externally applied force A is applied to the elongate shaft portion of the plunger rod, along longitudinal axis 34 in the direction of the stopper, it creates a force component B which is directed substantially outwardly from the interface of forward tapered plunger rod wall 36 and forward tapered annular inside wall 55. As a result of force component B annular exterior front rib 49 applies more sealing pressure to the syringe barrel cylindrical inside wall than the initial pressure existing as a result of the front rib being larger than the syringe barrel inside wall. Simultaneously, a force component C of applied force A moves the stopper and the fluid contained in the syringe along the syringe barrel toward the distal end of the syringe.

When force D is applied to the elongate shaft portion along longitudinal axis 34 in a direction away from the stopper, as seen in FIG. 9, it creates a force component E which is directed substantially outwardly from the interface of rear tapered plunger rod wall 37 and rear tapered annular inside wall 56. As a result of force component E annular exterior rib 51 applies more sealing pressure to the syringe barrel cylindrical inside wall than the initial pressure existing as a result of rear rib 51 being larger than the syringe barrel cylindrical inside wall. At the same time, a force component F of applied force D moves the stopper along the syringe barrel away from the distal end of the syringe thus drawing fluid into the syringe. An interior facing annular ring 23 in the syringe barrel is adapted to engage a step portion 33 on the plunger rod to help prevent the inadvertent removal of the plunger rod assembly from the syringe barrel while filling the syringe with medication.

It is preferred that front wall 47 of the stopper be concavely shaped and include a rigid center section 57 and a thinner radially projecting concave front wall portion 59, as more clearly illustrated in FIG. 5. When fluid is being drawn into the syringe a low pressure area is created within the interior of the syringe barrel. The resulting suction force, shown as force component L in FIG. 9, will pull on front wall 47. With the concave structure the suction force pulls on center section 57 which produces a compression force in concave front wall portion 59 which in turn increases the sealing pressure being applied by exterior front rib 49 to the syringe barrel cylindrical inside wall.

It is also preferred that front inside surface 54 of the stopper be adjacent to front portion 35 of the plunger rod. When fluid is being expelled from the syringe, front portion 35 presses against concave center section 57 of the flexible stopper. This pressing force is shown as force component H in FIG. 8. Component H forces the center section outwardly which produces a compression force in concave front wall portion 59 which in turn increases the sealing pressure being applied by exterior front rib 49 to the syringe barrel cylindrical inside wall.

Figure 11:
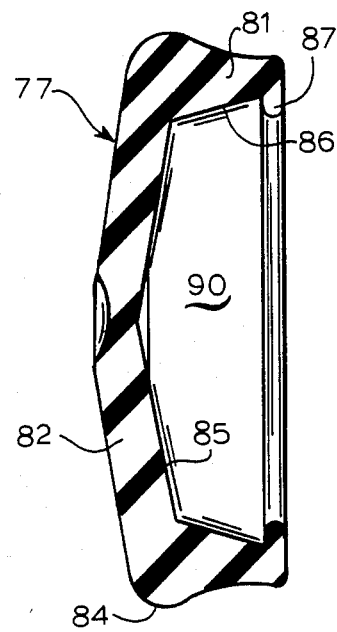
FIG. 11 is an enlarged cross-sectional view of a stopper adapted to fit the plunger rod of FIG. 10.
Figure 12:
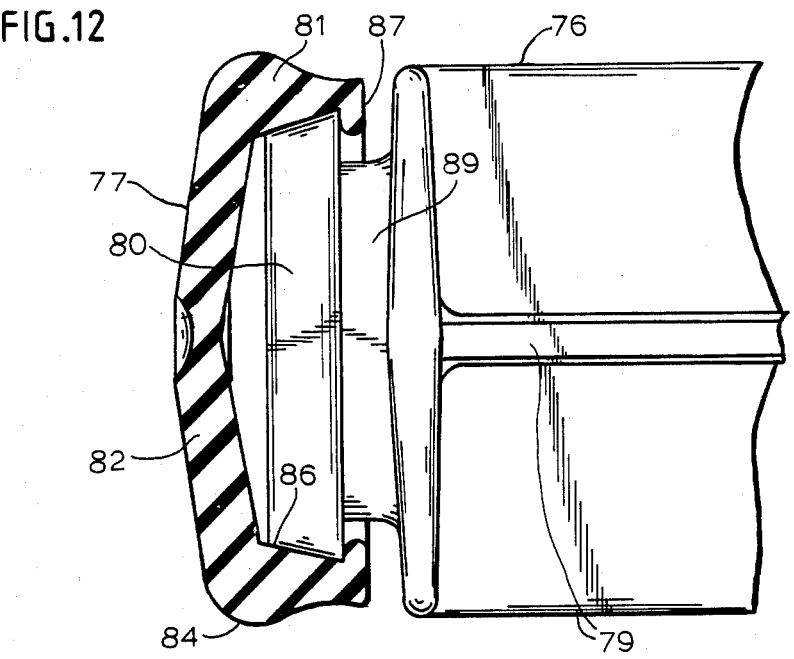
FIG. 12 is an enlarged partial cross-sectional view of an alternative plunger rod assembly using the plunger rod of FIG. 10 and the stopper of FIG. 11.
Figure 14:
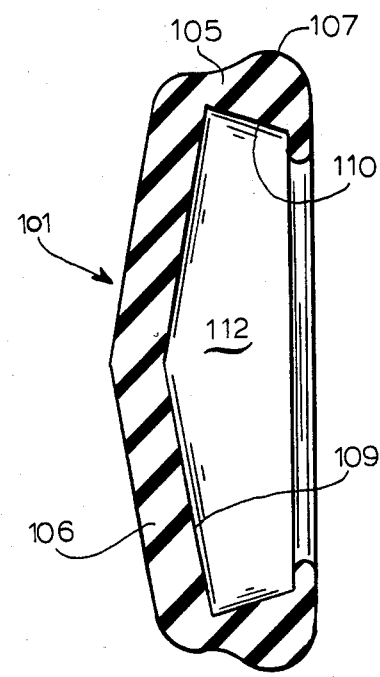
FIG. 14 is an enlarged cross-sectional view of a stopper adapted to fit the plunger rod FIG. 13.

There are cases where a convexly shaped stopper, as shown in FIGS. 11, 12 and 14, is required to reduce the amount of medication lost in the syringe. However, in these cases the suction force encountered when fluid is being drawn into the syringe will pull on the front wall of a convexly shaped stopper tending to pull the exterior front rib away from the syringe barrel cylindrical inside wall. This tendency can be minimized by increasing the stiffness of the stopper front wall by making it thicker or by supplying internal structural ribs. Also, medication loss may be reduced in the concave stopper structure by enlarging the rigid center section in a direction along the stopper longitudinal axis.

It is preferred that both forward tapered plunger rod wall 36 and rear tapered plunger rod wall 37 have a substantially continuous smooth surface so that outwardly directed forces B and E, respectively, are transmitted uniformly to the stopper ribs, thus tending to provide uniform sealing pressure between the stopper ribs and the cylindrical inside wall.

Figure 10:
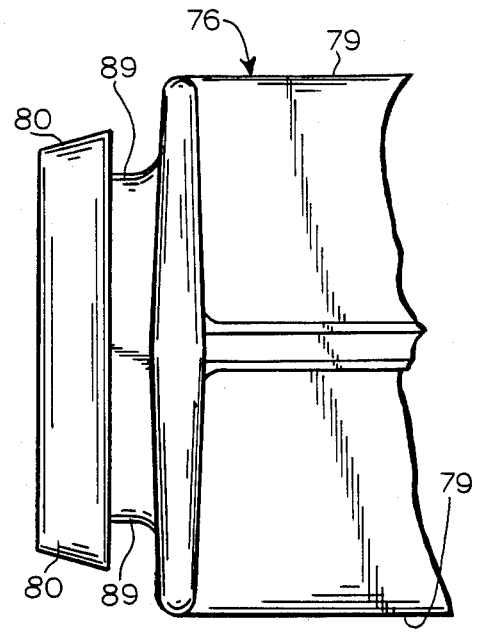
FIG. 10 is an enlarged side elevation view of the distal end of a plunger rod of an alternative embodiment of a plunger rod assembly of the present invention.

FIGS. 10-12 show an alternative embodiment of the plunger rod assembly of the present invention. This embodiment is similar to the previously described preferred embodiment except that the plunger rod tip and the stopper inside wall are only tapered in one direction. Here the plunger rod assembly comprises a plunger rod 76 and a flexible cup-shaped stopper 77. Plunger rod 76 includes a rigid elongate shaft portion 79 having a circular tapered tip portion 80 at the distal end thereof. The tapered tip is smallest at the distal end of the plunger rod and is tapered outwardly along the elongate shaft portion.

Stopper 71 includes an annular side wall 81, a front wall 82 connected to the side wall, and an exterior surface 84 of the annular side wall which is larger in diameter than the receptacle inside wall. The interior of stopper 77 includes an inside surface 85 of front wall 82, a tapered annular inside wall 86 connected to the annular side wall and the inside surface. Tapered annular inside wall 86 and inside surface 85 define a cavity 90 which has the tapered tip portion received therein as can be seen in FIG. 12. Tapered annular inside wall 86 is inclined at approximately the same angle as tapered tip portion 80 and is adjacent thereto, when assembled. When the plunger rod assembly of this embodiment is placed in a receptacle, such as a syringe, and a driving force is applied along elongate shaft portion 79 in the direction of stopper 77, a force component is created. This force component is directed substantially outwardly from the interface of tapered tip portion 80 and tapered annular inside wall 86, in a manner similar to the previously described embodiment. The result is that exterior surface 84 applies more sealing pressure to the receptacle inside wall than the pressure existing as a result of the exterior surface being larger than the receptcle inside wall. Simultaneously, a component of the applied driving force along the elongate shaft portion in the direction of the stopper moves the stopper and the fluid contained in the receptacle in the direction of this force component. No outwardly directed force component is created unless the plunger rod assembly is in a receptacle which offers resistance to the motion of the stopper. This resistance will be created by making the receptacle inside diameter smaller than the stopper outside diameter.

In order to maintain the positional relationship of the stopper and the plunger rod and to hold tapered tip portion 80 adjacent to tapered annular inside wall 86 flexible flange 87 and groove 89 are provided. Flexible flange 87 is connected to and extends inwardly from annular side wall 81 at the end opposite front wall 82. Groove 89 in the plunger rod is sized and shaped to accept flange 87 which is received therein. The groove is positioned inwardly adjacent to tapered tip portion 80.

Figure 13:
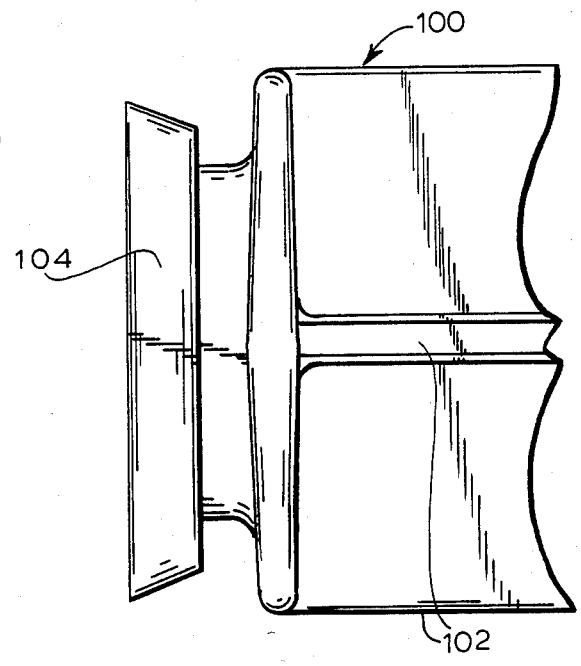
FIG. 13 is an enlarged side elevation view of the distal end of a plunger rod of another alternative embodiment of a plunger rod assembly of the present invention.

FIGS. 13-14 show another alternative embodiment of the plunger rod assembly of the present invention. This alternative embodiment is similar to the embodiment described by FIGS. 10-12 except that, as will be described, the direction of the tapered surfaces is reversed. Here the plunger rod assembly consists of a plunger rod 100 and a flexible cup-shaped stopper 101. Plunger rod 100 includes a rigid elongate shaft portion 102 having a circular tapered tip portion 104 at the distal end thereof. The diameter of the tapered tip is largest at the distal end of the plunger rod and is tapered inwardly along the elongate shaft portion.

Stopper 101 includes an annular side wall 105, a front wall 106 connected to the side wall, and an exterior surface 107 of the annular side wall which is larger in diameter than the inside wall of a receptacle, such as a syringe, into which the stopper fits. The interior of stopper 101 includes an inside surface 109 of front wall 106, a tapered annular inside wall 110 connected to the annular side wall and the inside surface. Tapered annular inside wall 110 and inside surface 109 define a cavity 112. The assembly of plunger rod 100 and stopper 101 is not shown, but is similar to the previous embodiments. When these components are assembled cavity 112 has tapered tip portion 104 received therein. Tapered annular inside wall 110 is inclined at approximately the same angle as tapered tip portion 104 and is adjacent thereto. When the receptacle, such as a syringe, and when a driving force is applied along the elongate shaft portion, in a direction away from the stopper, exterior surface 107 applies more pressure to the receptacle inside wall than the pressure existing as a result of the exterior surface being larger than the receptacle inside wall.

Although the plunger rod assembly of the present invention is being described for use with a circular syringe barrel or circular receptacle it is understood that the principles of the present invention also apply for a use in a noncircular receptacle or barrel.

Syringe barrels are usually made of plastic such as polypropylene or glass. It is common practice to lubricate the interior of the syringe barrel and/or the exterior of known stoppers with medical grade lubricant such as silicone lubricant. The lubricant allows the stopper to move freely along the interior of the barrel even when there is no liquid in the interior of the syringe barrel. The plunger rod may be constructed of a wide variety of materials since, in most applications, adequate strength and reasonable cost are the major considerations. Possible plunger rod materials include polypropylene and polystyrene. Certain thermoplastic materials, having a durometer reading of from 30 to 90 on the Shore A scale, may be used in manufacturing a thermoplastic stopper. Preferred stopper materials include, but are not limited to, polyurethane, polyolefin elastomers and polyamide block amide. Since the plunger rod assembly of this invention is preferably sterile, when used in medical applications, all materials should be chosen to accommodate the sterilization process.

Thus, there has been provided in accordance with the present invention a method and an apparatus for moving fluid along a conduit and more particularly a variable sealing pressure plunger rod assembly useful in a syringe in which the stopper may be constructed of thermoplastic material.

What is claimed is:

1. A plunger rod assembly for use with a syringe barrel having a cylindrical inside wall and provided with a proximal open end to receive the plunger rod assembly and a distal end adapted to receive and be in fluid communication with fluid delivery means comprising:

a plunger rod including a rigid elongate shaft portion having a circular tapered tip portion at the distal end thereof, said shaft portion being sufficiently long as to be accessible outside of the syringe barrel;

a flexible thermoplastic stopper including an annular side wall circumscribing a longitudinal axis, a continuous front wall intersecting said longitudinal axis and being integral with said side wall, an annular rib being larger in diameter than said side wall and being integral with said side wall, said rib being larger in diameter than the syringe barrel cylindrical inside wall, an inside surface of said front wall, a tapered annular inside wall extending from said inside surface and being integral with said side wall, said tapered annular inside wall and said inside surface defining a cavity which has said tapered tip portion received therein, said tapered annular inside wall having a substantially continuous smooth surface, said tapered annular inside wall being inclined at approximately the same angle as said tapered tip portion and adjacent thereto whereby force applied to said shaft portion in the direction of descending taper of said tapered tip portion creates a force component which is directed substantially outwardly from the interface of said tapered tip portion and said tapered annular inside wall wherein said rib applied more pressure to the syringe barrel cylindrical wall than the initial pressure existing as a result of said rib being larger than the syringe barrel inside wall; and cooperating means for maintaining the positional relationship of said stopper and said plunger rod.

2. A plunger rod assembly for use with a receptacle having an inside wall and provided with means for receiving the plunger rod assembly and means for fluid communication with the exterior of the receptacle:

a plunger rod including a rigid elongate shaft portion having a tapered tip portion at the distal end thereof;

a flexible cup-shaped thermoplastic stopper including an annular side wall, a continuous front wall connected to said side wall, an exterior surface of said annular side wall being larger in diameter than the receptacle inside wall, an inside surface of said front wall, a tapered annular inside wall connected to said annular side wall, said tapered annular inside wall and said inside surface being connected and defining a cavity which has said tapered tip portion received therein, said tapered annular inside wall having substantially continuous smooth surface, said tapered annular inside wall being inclined at approximately the same angle as said tapered tip portion and adjacent thereto whereby force applied to said shaft portion in the direction of descending taper of said tapered tip portion creates a force component which is directed substantially outwardly from the interface of said tapered tip portion and said tapered annular inside wall wherein said exterior surface applies more pressure to the receptacle inside wall than the initial pressure existing as a result of said exterior surface being larger than the receptacle inside wall; and cooperating means for maintaining the positional relationship of said stopper and said plunger rod.

3. A plunger rod assembly for use with a syringe barrel having a cylindrical inside wall and provided with a proximal open end to receive the plunger rod assembly and a distal end adapted to receive and be in fluid communication with fluid delivery means comprising:

a plunger rod including a elongate shaft portion defining a longitudinal axis, a front portion at the distal end of said shaft portion, a circular forward tapered plunger rod wall intersecting said front portion and tapering outwardly from said intersection along said longitudinal axis, a circular rear tapered plunger rod wall connected to said forward tapered plunger rod wall and tapering inwardly from said connection along said longitudinal axis, a rear portion of said rear tapered plunger rod wall being substantially in a plane intersecting said longitudinal axis, said elongate shaft portion being sufficiently long as to be accessible outside of the syringe barrel;

a thermoplastic stopper including an annular side wall circumscribing a stopper longitudinal axis, a front wall intersecting said stopper longitudinal axis and being integral with said side wall, an annular exterior front rib formed at the intersection of said front wall and said side wall, an annular rear edge at the end opposite said front wall and being integral with said annular side wall, an annular exterior rear rib formed at the intersection of said side wall and said rear edge, said front rib and said rear rib being larger in diameter than the syringe barrel inside wall, an annular exterior recess positioned between and being of smaller diameter than said front rib and said rear rib, a front inside surface of said front wall, a forward tapered annular inside wall intersecting said front inside surface and being tapered outwardly from said intersection along said stopper longitudinal axis, said forward tapered annular inside wall being integral with said side wall, said forward tapered annular inside wall being inclined at approximately the same angle as said forward tapered plunger rod wall and adjacent thereto whereby force applied to said elongate shaft portion along said longitudinal axis in the direction of said stopper creates a force component which is directed substantially outwardly from the interface of said forward tapered plunger rod wall and said forward tapered annular inside wall wherein said annular exterior front rib applies more sealing pressure to the syringe barrel cylindrical wall than the initial pressure existing as a result of said front rib being larger than the syringe barrel inside wall, a rear tapered annular inside wall connected to said forward tapered annular wall and being tapered inwardly from said connection along said longitudinal axis and terminating at said rear edge, said rear tapered annular inside wall being integral with said side wall, said rear tapered annular wall being inclined at approximately the same angle as said rear tapered plunger rod wall and adjacent thereto whereby force applied to said elongate shaft portion along its longitudinal axis in a direction away from said stopper creates a force component which is directed substantially outwardly from the interface of said rear tapered plunger rod wall and said rear tapered annular inside wall wherein said annular exterior rear rib applies more sealing pressure to the syringe barrel cylindrical wall than the initial pressure existing as a result of said rear rib being larger than the syringe barrel inside wall.

4. The plunger rod assembly of claim 3 wherein said front portion of said plunger rod is a flat surface in a plane substantially perpendicular to said longitudinal axis.

5. The plunger rod assembly of claim 4 wherein said front wall is concavely shaped.

6. The plunger rod assembly of claim 5 wherein said front inside surface of said front wall is adjacent to said front portion.

7. The plunger rod assembly of claim 3 wherein said forward tapered plunger rod wall has a substantially continuous smooth surface.

8. The plunger rod assembly of claim 3 wherein said rear tapered plunger rod wall has a substantially continuous smooth surface.

9. The plunger rod assembly of claim 3, wherein an undercut neck portion is connected to said rear portion of said rear tapered plunger rod wall, said undercut neck portion being smaller in diameter than the smallest diameter of said rear tapered plunger rod wall and being positioned substantially symmetrically around said longitudinal axis.

10. A plunger rod for use as a component in a syringe assembly comprising:

a rigid elongate shaft portion defining a longitudinal axis;

a front portion at the distal end of said shaft portion;

a circular forward tapered plunger rod wall intersecting said front portion and tapering outwardly from said intersection along said longitudinal axis;

a circular rear tapered plunger rod wall connected to said forward tapered plunger rod wall and tapering inwardly from said connection along said longitudinal axis;

a rear portion of said rear tapered plunger rod wall being substantially in a plane intersecting said longitudinal axis; and an undercut neck portion connected to said rear portion.

11. The plunger rod of claim 10 wherein said front portion is a flat surface in a plane substantially perpendicular to said longitudinal axis.

12. The plunger rod of claim 10 wherein said forward tapered plunger rod wall has a substantially continuous smooth surface.

13. The plunger rod of claim 10 wherein said rear tapered plunger rod wall has a substantially continuous smooth surface.

14. The plunger rod of claim 11 which further includes:

a disc-shaped member attached to the proximal end of said shaft portion, said disc being substantially perpendicular to said longitudinal axis, said disc being larger in diameter than the largest dimension of said shaft portion taken in a plane perpendicular to said longitudinal axis.

15. A thermoplastic stopper for use on a plunger rod comprising:

an annular side wall circumscribing a stopper longitudinal axis;

a front wall intersecting said longitudinal axis and being integral with said side wall;

an annular exterior front rib formed at the intersection of said front wall and said side wall;

an annular rear edge at the end opposite said front wall and being integral with said annular side wall;

an annular exterior rear rib formed at the intersection of said side wall and said rear edge;

an annular exterior recess positioned between and being of smaller diameter than said front rib and said rear rib;

a front inside surface of said front wall;

a forward tapered annular inside wall intersecting said front inside surface and being tapered outwardly from said intersection along said longitudinal axis, said forward tapered annular inside wall being integral with said side wall; and a rear tapered annular inside wall connected to said forward tapered annular inside wall and being tapered inwardly from said connection along said longitudinal axis and terminating at said rear edge, said rear tapered annular inside wall being integral with said side wall.

16. The stopper of claim 15 wherein said front wall is concavely shaped.

17. The stopper of claim 15 wherein said front wall is convexly shaped.

18. The stopper of claim 17 wherein said thermoplastic material is selected from the group consisting of polyurethane, polyolefin elastomers and polyamide block amide.

19. A syringe assembly comprising:

a syringe barrel having a cylindrical inside wall, an open end at the proximal end of said barrel, a distal end adapted to receive and be in fluid communication with fluid delivery means;

a plunger rod including a rigid elongate shaft portion having a circular tapered tip portion at the distal end thereof, said shaft portion being sufficiently long as to be accessible outside of said syringe barrel;

a flexible thermoplastic stopper contained within said syringe barrel, said stopper including an annular side wall circumscribing a longitudinal axis, a continuous front wall intersecting said longitudinal axis and being integral with said side wall, an annular rib being larger in diameter than said side wall and being integral with said side wall, said rib being larger in diameter than said syringe barrel cylindrical inside wall, an inside surface of said front wall, a tapered annular inside wall extending from said inside surface and being integral with said side wall, said tapered annular inside wall and said inside surface defining a cavity which has said tapered tip portion received therein, said tapered annular inside wall being inclined at approximately the same angle as said tapered tip portion and adjacent thereto whereby force applied to said shaft portion in the direction of descending taper of said tapered tip portion creates a force component which is directed substantially outwardly from the interface of said tapered tip portion and said tapered annular inside wall wherein said rib applies more pressure to said syringe barrel cylindrical wall, than the initial pressure existing as a result of said rib being larger than said syringe barrel inside wall; and cooperating means for maintaining the positional relationship of said stopper and said plunger rod.

20. The assembly of claims 1, 2 or 19 wherein the cooperating means for maintaining the positional relationship of said stopper and said plunger rod comprises:

a flexible flange connected to and extending inwardly from said annular side wall at the end opposite said front wall; and a groove in said plunger rod sized and shaped to accept said flange which is received therein, said groove positioned inwardly adjacent to said tapered tip portion, said flange and said groove being engaged for holding said tapered tip portion adjacent to said tapered annular inside wall.

21. The assembly of claims 1, 2 or 19 wherein said tapered tip portion has a substantially continuous smooth surface.

22. The assembly of claims 1, 2, 3 or 19 wherein said front wall of said stopper is concavely shaped.

23. The assembly of claims 1, 2, 3 or 19 wherein said front wall of said stopper is convexly shaped.

24. The syringe assembly of claim 19 wherein said cylindrical inside wall is coated with medical grade silicone lubricant.

25. The assembly of claim 1, 2, 3 or 19 wherein said thermoplastic material is selected from the group consisting of polyurethane, polyolefin elastomers and polyamide block amide.

26. A method of expelling fluid from a syringe assembly of the type including: a barrel having an inside wall, a proximal end to receive a plunger rod assembly and a distal end in fluid communication with the exterior of the syringe; an elongate plunger rod defining a longitudinal axis with a tapered tip at one end thereof, said tapered tip being smallest at the distal end of said plunger rod and tapering outwardly along said longitudinal axis; and a flexible cup-shaped thermoplastic stopper including an annular side wall, a continuous front wall connected to said side wall, an exterior surface of said annular side wall being larger in diameter than said syringe barrel inside wall, a tapered annular inside wall connected to said annular side wall, said tapered annular inside wall being inclined at approximately the same angle as said tapered tip and adjacent thereto comprising:

applying a driving force along said elongate plunger rod in the direction of descending taper of said tapered tip whereby said force creates a force component which is directed substantially outwardly from the interface of said tapered tip and said tapered annular inside wall wherein said exterior surface applies more sealing pressure to said syringe barrel inside wall than the pressure existing as a result of said exterior surface being larger than said syringe barrel inside wall while a component of said applied driving force along said plunger rod moves said stopper and the fluid contained in said syringe along said barrel to the exterior of said syringe.

27. An apparatus for moving fluid along the inside of a circular conduit comprising:

a plunger rod including a rigid elongate shaft portion having a tapered tip portion at the distal end thereof; and a flexible cup shaped thermoplastic stopper including an annular side wall, a continuous front wall connected to said side wall, an exterior surface of said annular side wall being larger in diameter than the inside wall of the circular conduit, an inside surface of said front wall, a tapered annular inside wall connected to said annular side wall, said tapered annular inside wall and said inside surface being connected and defining a cavity which has said tapered tip portion received therein, said tapered annular inside wall being inclined at approximately the same angle as said tapered tip portion and adjacent thereto whereby force applied to said shaft portion in the direction of descending taper of said tapered tip portion creates a force component which is directed substantially outwardly from the interface of said tapered tip portion and said tapered annular inside wall wherein said exterior surface applies more pressure to the inside of the circular conduit than the initial pressure existing as a result of said exterior surface being larger than the inside of the circular conduit.

\* \* \* \* \*